(12) United States Patent
Richter et al.

(10) Patent No.: US 9,034,039 B2
(45) Date of Patent: May 19, 2015

(54) INTERVERTEBRAL IMPLANT WITH ELASTIC PART

(75) Inventors: Marcus Richter, Wiesbaden (DE); Nicolas Willmann, Ulm (DE); Sven Hamich, Ulm (DE)

(73) Assignee: ULRICH GMBH & CO.KG, Ulm (DE)

( * ) Notice: Subject to any disclaimer, the term of this patent is extended or adjusted under 35 U.S.C. 154(b) by 810 days.

(21) Appl. No.: 12/522,181

(22) PCT Filed: Jan. 16, 2008

(86) PCT No.: PCT/DE2008/000072
§ 371 (c)(1),
(2), (4) Date: Jul. 29, 2009

(87) PCT Pub. No.: WO2008/106912
PCT Pub. Date: Sep. 12, 2008

(65) Prior Publication Data
US 2010/0016969 A1  Jan. 21, 2010

(30) Foreign Application Priority Data
Mar. 7, 2007 (DE) .......................... 10 2007 011 059

(51) Int. Cl.
*A61F 2/44* (2006.01)
*A61F 2/30* (2006.01)

(52) U.S. Cl.
CPC .............. *A61F 2/44* (2013.01); *A61F 2/30744* (2013.01); *A61F 2/442* (2013.01); *A61F 2002/30006* (2013.01); *A61F 2002/30235* (2013.01); *A61F 2002/30405* (2013.01); *A61F 2002/30471* (2013.01); *A61F 2002/30495* (2013.01); *A61F 2002/3055* (2013.01); *A61F 2002/30563* (2013.01); *A61F 2002/30566* (2013.01); *A61F 2002/30571* (2013.01); *A61F 2002/30578* (2013.01); *A61F 2002/30594* (2013.01); *A61F 2002/30601* (2013.01); *A61F 2002/30841* (2013.01); *A61F 2002/4475* (2013.01); *A61F 2220/0025* (2013.01);
(Continued)

(58) Field of Classification Search
CPC ...... A61F 2/44; A61F 2/442; A61F 2002/443
USPC ........................................... 623/17.11–17.16
See application file for complete search history.

(56) References Cited

U.S. PATENT DOCUMENTS 4,608,053 A * 8/1986 Keller ......................... 623/23.31
5,320,644 A  6/1994 Baumgartner .................. 623/17
5,571,192 A  11/1996 Schonhoffer ............... 623/17.11
(Continued)

FOREIGN PATENT DOCUMENTS

DE  20019520  3/2001
EP  0985384 A1  3/2000
(Continued)

*Primary Examiner* — Jerry Cumberledge
*Assistant Examiner* — Nicholas Plionis
(74) *Attorney, Agent, or Firm* — Andrew Wilford

(57) ABSTRACT

The invention relates to an implant for the insertion between vertebral bodies (2) of the spinal column, having a first contact surface (9) for the disposition on one of the adjacent vertebral bodies (2), and a second contact surface (10) for the disposition on the implant part (3, 4) comprising the other adjacent vertebral body (2). At least one elastically flexible component (11) is disposed in the force transmission chain formed by the implant part (3, 4) between the disposition surfaces of the adjacent vertebral bodies (2).

8 Claims, 5 Drawing Sheets

(52) U.S. Cl.
CPC  *A61F 2220/0091* (2013.01); *A61F 2230/0069* (2013.01); *A61F 2250/0015* (2013.01)

(56) References Cited

U.S. PATENT DOCUMENTS

| | | | |
|---|---|---|---|
| 5,827,328 | A | 10/1998 | Buttermann |
| 6,136,031 | A | 10/2000 | Middleton ............... 623/17 |
| 6,143,031 | A * | 11/2000 | Knothe et al. ............ 623/17.16 |
| 6,200,348 | B1 | 3/2001 | Biedermann |
| 6,296,664 | B1 | 10/2001 | Middleton |
| 6,395,035 | B2 | 5/2002 | Bresina et al. |
| 6,579,321 | B1 | 6/2003 | Gordon et al. |
| 6,582,468 | B1 | 6/2003 | Gauchet |
| 6,752,832 | B2 | 6/2004 | Neumann ............... 623/17.15 |
| 6,808,538 | B2 * | 10/2004 | Paponneau ............... 623/17.16 |
| 7,758,646 | B2 | 7/2010 | Khandkar |
| 2001/0016774 | A1 * | 8/2001 | Bresina et al. ............ 623/17.15 |
| 2001/0051829 | A1 | 12/2001 | Middleton ............... 623/17.16 |
| 2004/0186569 | A1 * | 9/2004 | Berry ...................... 623/17.11 |
| 2004/0210312 | A1 | 10/2004 | Neumann |
| 2004/0220671 | A1 | 11/2004 | Ralph et al. ............ 623/17.15 |
| 2005/0004572 | A1 | 1/2005 | Biedermann et al. ............ 606/61 |
| 2005/0113924 | A1 | 5/2005 | Buttermann ............. 623/17.13 |
| 2005/0187627 | A1 | 8/2005 | Ralph et al. ............ 623/17.11 |
| 2006/0058877 | A1 * | 3/2006 | Gutlin et al. ............ 623/17.11 |
| 2006/0089714 | A1 * | 4/2006 | Liu et al. .................. 623/17.15 |
| 2006/0100710 | A1 * | 5/2006 | Gutlin et al. ............ 623/17.15 |
| 2006/0116767 | A1 | 6/2006 | Magerl et al. |
| 2006/0116769 | A1 * | 6/2006 | Marnay et al. ............ 623/17.15 |
| 2006/0178744 | A1 * | 8/2006 | de Villiers et al. ........ 623/17.13 |
| 2006/0200240 | A1 * | 9/2006 | Rothman et al. ........ 623/17.13 |
| 2006/0282166 | A1 | 12/2006 | Molz |
| 2007/0050032 | A1 * | 3/2007 | Gittings et al. ........... 623/17.12 |
| 2007/0179618 | A1 * | 8/2007 | Trieu et al. ................ 623/17.14 |

FOREIGN PATENT DOCUMENTS

| | | | |
|---|---|---|---|
| FR | | 2734148 A | 11/1996 |
| WO | WO 2005039454 A2 * | | 5/2005 |
| WO | WO 2005039455 | | 5/2005 |

* cited by examiner

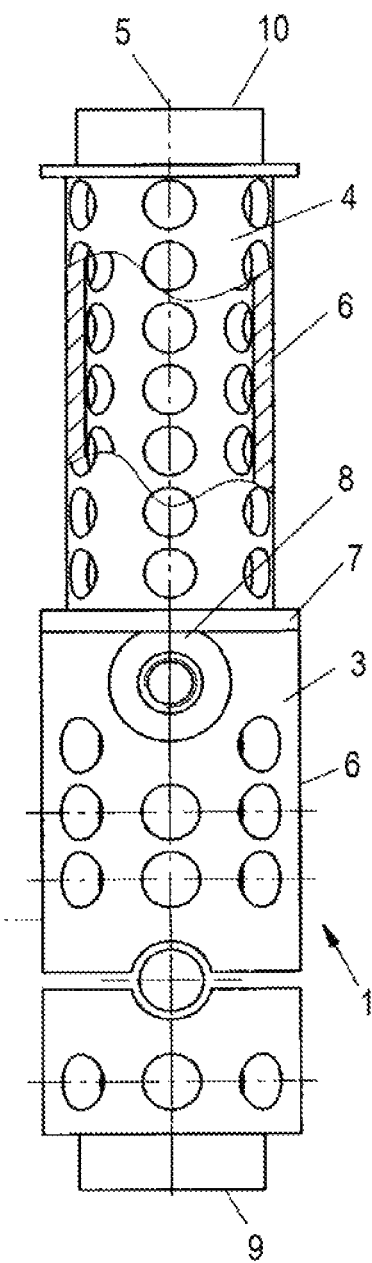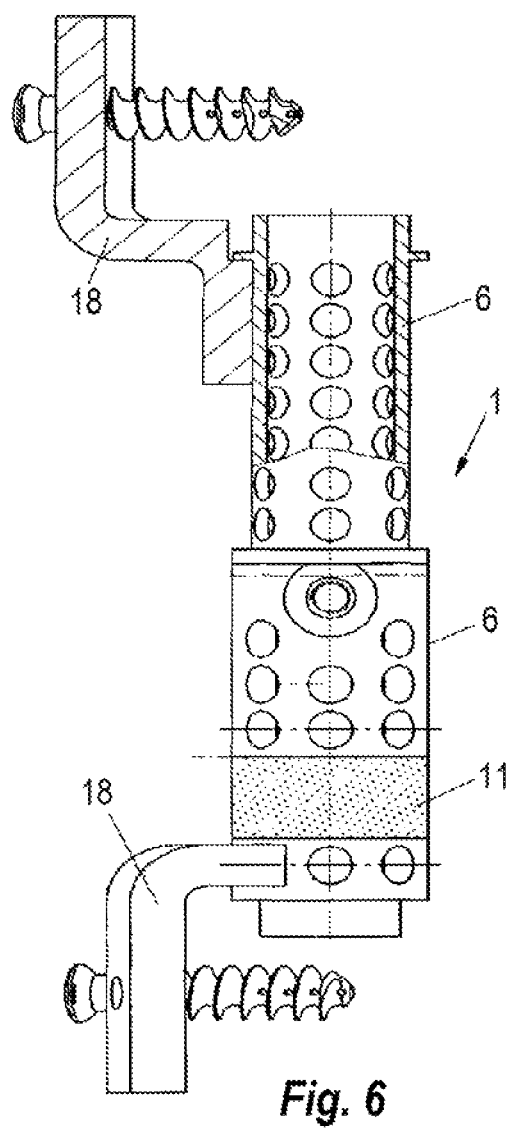
Fig. 5
Fig. 6

INTERVERTEBRAL IMPLANT WITH ELASTIC PART

CROSS REFERENCE TO RELATED APPLICATIONS

This application is the US national phase of PCT application PCT/DE2008/000072, filed 16 Jan. 2008, published 12 Sep. 2008 as WO2008/106912, and claiming the priority of German patent application 102007011059.8 itself filed 7 Mar. 2007, whose entire disclosures are herewith incorporated by reference.

BACKGROUND OF THE INVENTION

The invention relates to an implant for installation between vertebrae of the spinal column, with an implant part having a first contact surface for bearing against one of the adjacent vertebrae and a second contact surface for bearing against the other adjacent vertebral body.

Implants of this type are known, for example, from DE 44 23 257 [U.S. Pat. No. 5,571,192] that describes a possible basic structure of the implant according to the invention. The same also applies to EP 1 721 583 [U.S. Pat. No. 6,752,832] that discloses an implant whose structure is suitable as a starting point for the invention.

With known implants to be inserted between the vertebrae of the spinal column, there is the problem with the embodiments hitherto known from the prior art that overloading of the vertebral end plates can occur, with the result that it can fracture and the vertebrae adjacent to the implant are thus also damaged or even destroyed.

OBJECT OF THE INVENTION

The object of the invention is therefore to provide an implant of the type described above such that the strain on the vertebral end plates is reduced.

SUMMARY OF THE INVENTION

This object is attained according to the invention with an implant of the type described above in that at least one elastically compressible part is arranged between the bearing surfaces of the adjacent vertebrae in the force-transmission chain formed by the implant part.

This design results in the advantage that a uniform distribution of the load is achieved on the bearing surface of the vertebral end plates of the adjacent vertebrae, since the implant can adapt to the orientation of the bearing surfaces is made possible by the elastically compressible part. The contact surface is thereby enlarged and in particular one-sided line contact avoided, so that caving-in of the vertebral end plates cannot occur locally with a subsequently spreading break. The improved bearing of the implant parts against the adjacent vertebrae thereby also includes a configuration in which the implant part bends at in the elastically compressible part, that is, in principle a pivot is provided that furthermore also takes over the function of the intervertebral disks and cushions load peaks or impacts.

Within the scope of the invention it is preferred that the at least one elastically compressible part is assigned to the first contact surfaces and/or to the second contact surface, since uniform force distribution on the implant parts at the ends is thus realized, that is, in principle already known implant parts can be supplemented and further developed by the features according to the invention without having to change their basic construction.

There is thus the possibility thereby the elastically compressible part is formed from a solid elastic body, that is the elasticity is a property of the body. The behavior can be influenced in that lamellae are formed in the solid elastic body, the number, arrangement and design of the lamellae offering further parameters for the variation of its elasticity.

Alternatively, it is possible that the elastically compressible part is itself elastic, that is the material itself does not need to have the elastic properties in order to thus avoid a limitation of the material selection. As an example of a suitable elastic configuration of a material that is itself relatively rigid, reference can be made to a metal leaf spring.

It is very particularly preferred within the scope of the invention if several of the elastically compressible parts are provided distributed uniformly over the first contact surface and/or the second contact surface. With this design a uniform distribution of the load is achieved in a particularly simple manner, while at the same time making it possible to adjust to the locally given formations of the vertebral end plate, since each elastically compressible part can be deformed individually on its contact surface.

Furthermore, it is preferred within the scope of the invention if the implant part is formed as a tubular sleeve in whose wall the elastically compressible part is integrated. With this design, the elastically compressible part does not need to be positioned at the end of the implant part, which naturally additionally is likewise possible, but can release the end contact surfaces and provide the desired elasticity of the implant at any level along its longitudinal extension. There is therefore the possibility that the elastically compressible part is a honeycomb structure in the wall of the sleeve or that alternatively slots are formed in the wall of the sleeve in a crosswise offset arrangement. It is thereby suggested that two diametrically opposite slots are formed in a radial plane of the sleeve, the slots being offset by 90° to the longitudinal axis of the sleeve with respect to the slots in the adjacent radial planes, so that the desired elasticity can be produced subsequently by the formation of the slots in the wall of the sleeve. Another possibility is thereby given in that a coil spring is formed in the wall, but this is complex to produce with a one-part implant, so that in this case a multi-part embodiment seems logical.

In order to make individual adjustment of the implant possible for to the patients, end adapter plates are provided on the sleeve that form the first and second contact surfaces. There is also the possibility that the adapter plates form the elastically compressible parts so that as a result individual adjustment is made possible by a suitable selection of the design and material properties of the adapter plates.

Since the adapter plates can be produced separately from the sleeve, there is also the possibility of giving them density gradients extending longitudinally of the sleeve in order thus to achieve the desired elasticity.

Another alternative embodiment is characterized in that the adapter plates carry pins poking into a flexible pad, for bearing against the adjacent vertebrae so that a uniform bearing against the vertebral end plates is rendered possible in this manner.

It is possible to take into account the natural curvature of the spinal column when the end plates are hinged on the sleeve.

It is very particularly preferred within the scope of the invention if the implant part is formed in a multi-part manner with at least one first implant part and a second implant part that are adjustable with respect to one another along their longitudinal axis in order thus to create a traction option, that is, in a short configuration the implant can be simply inserted into the existing gap between the two vertebrae in order to be subsequently distracted in the course of the operation. The adjustability along the longitudinal axis can thereby be achieved in a particularly simple manner in that the first implant part and the second implant part are connected to one another by a distraction screwthread, reference can be made to the printed publications of the same applicant cited above for the making the distraction screwthread.

BRIEF DESCRIPTION OF THE DRAWING

The invention is explained in more detail below based on the illustrated embodiments shown in the drawing; therein:

FIG. 5 is a view like FIG. 1 of an embodiment with a pivot integrated in the wall of the sleeve and having a return spring, FIG. 6 is a view of the embodiment from FIG. 2 connected with brackets 18 engaging over the vertebrae.

DETAILED DESCRIPTION

Figure 10:
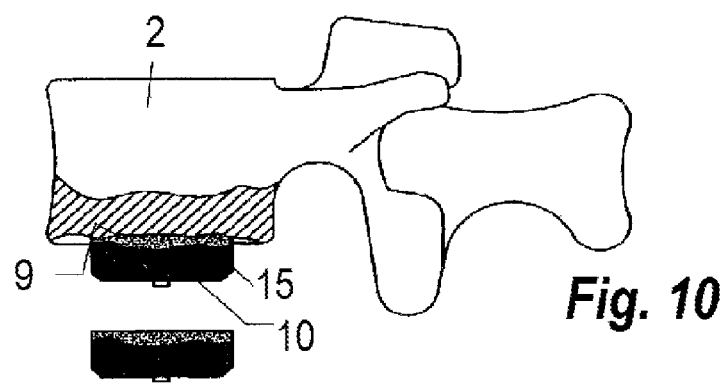
FIG. 10 is a diagrammatic view of an adapter plate with a density gradient extending longitudinally of the sleeve in contact with the bearing surface of the vertebral body.
Figure 11:
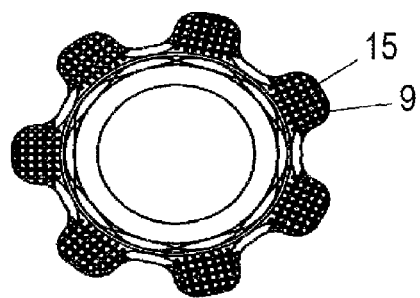
FIG. 11 is a view like FIG. 7 of another adapter plate.

The implant 1 shown in the drawing serves for installation between vertebrae 2 of the spinal column shown in the drawing itself only in FIG. 10. This implant 1 has a first implant part 3 and a second implant part 4 that are adjustable with respect to one another along their common longitudinal axis 5 in order to be able to change total length for distraction of the vertebrae 2. The first implant part 3 and the second implant part 4 are formed as tubular sleeves 6, the first implant part 3 surrounding the second implant part 4. A rotatable threaded ring 7 of the first implant part 3 has on its inner surface a screwthread engaged in a screwthread of the second implant part 4. On the outer surface the threaded ring 7 is provided at 8 with bevel or crown gear teeth in order to be able to be rotated and thus change total implant length by means of a surgical instrument engaging in the teeth.

Alternatively, there is also the possibility that the implant 1 has two end parts and one central part, the latter connected to the end implant parts via screwthreads of opposite hand. Although implants 1 of at least two implant parts 3 and 4 are always shown in the drawing to describe the illustrated embodiments, in principle the invention can be an implant 1 with only one implant part, but this then lacks the distraction possibility.

Figure 18:
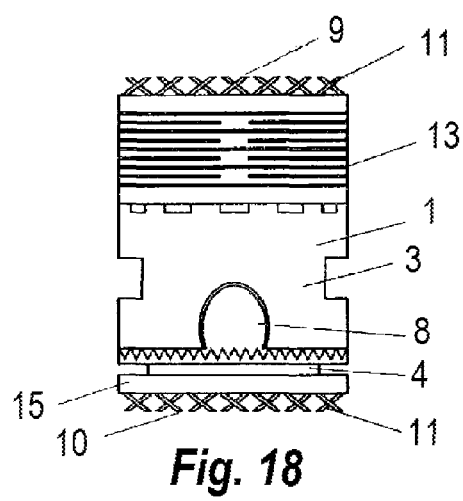
FIG. 18 is a side view of an implant according to the invention with slots formed in the wall of the sleeve in a crosswise offset arrangement and with elastically compressible parts elastically compressible on the first contact surface and on the second contact surface.

This one-part or multi-part implant part 3 and 4 has a first contact surface 9 for bearing against one of the adjacent vertebrae 2 and a second contact surface 10 for bearing against the other adjacent vertebral body, at least one part 11 being elastically compressible between the bearing surfaces of the adjacent vertebrae 2 in the force-transmission chain formed by the implant part 3 and 4, which part in the embodiment shown in FIG. 18 is provided several times on the first contact surface 9 as well as on the second contact surface 10.

Figure 1:
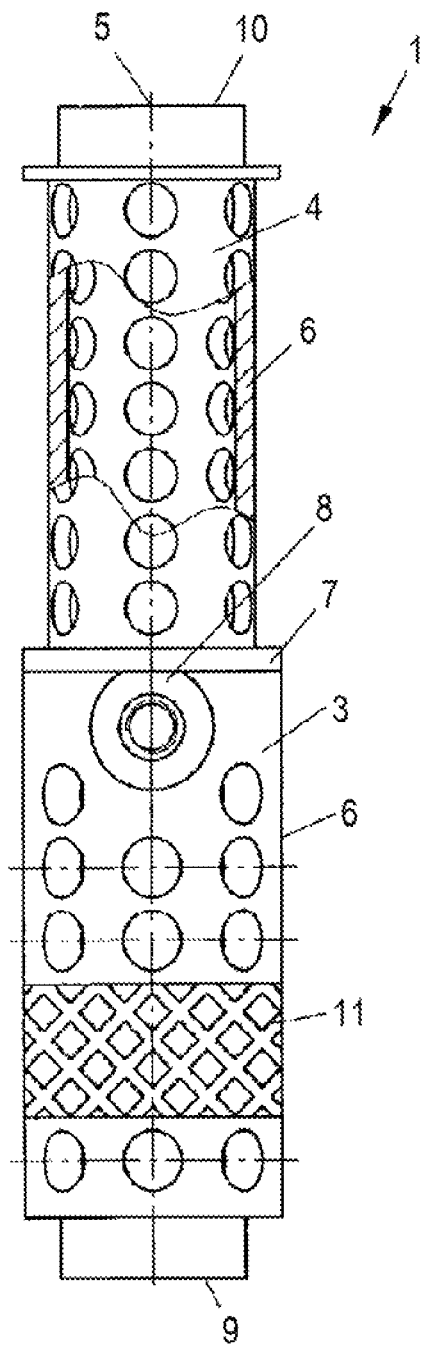
FIG. 1 is a side view of an implant according to the invention, shown partly in section with an elastically compressible part formed in the wall of the sleeve in a honeycomb structure.
Figure 2:
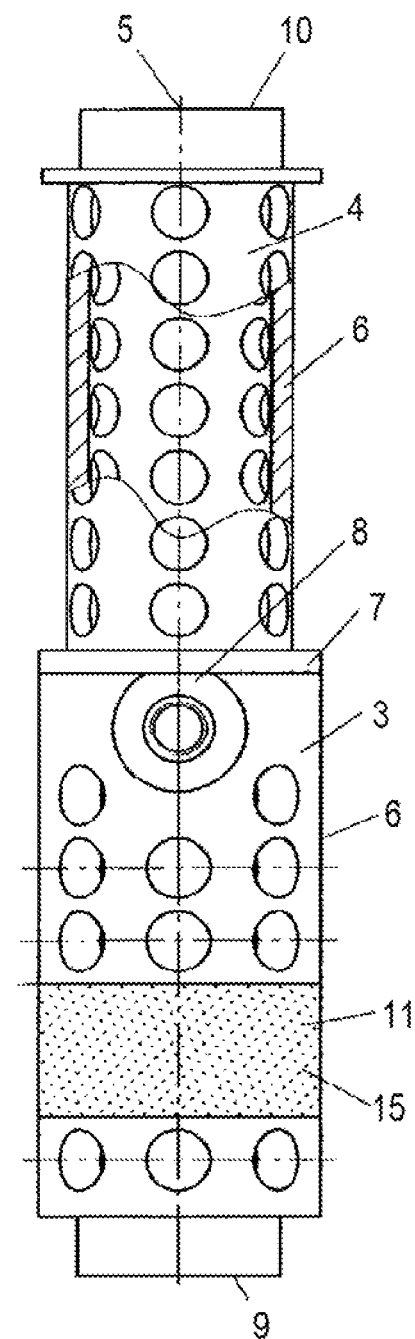
FIG. 2 is a view like FIG. 1 of another embodiment with an elastically compressible part of an elastically compact material integrated into the wall of the sleeve.
Figure 3:
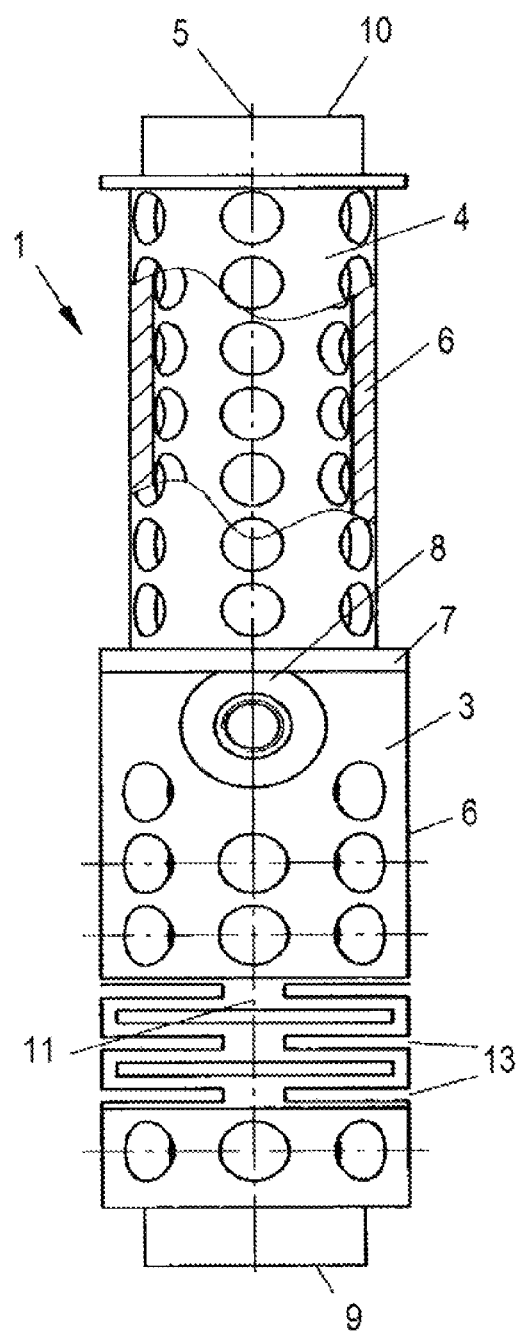
FIG. 3 is a view like FIG. 1 of an embodiment with a crosswise offset arrangement of slots formed in the wall of the sleeve.
Figure 4:
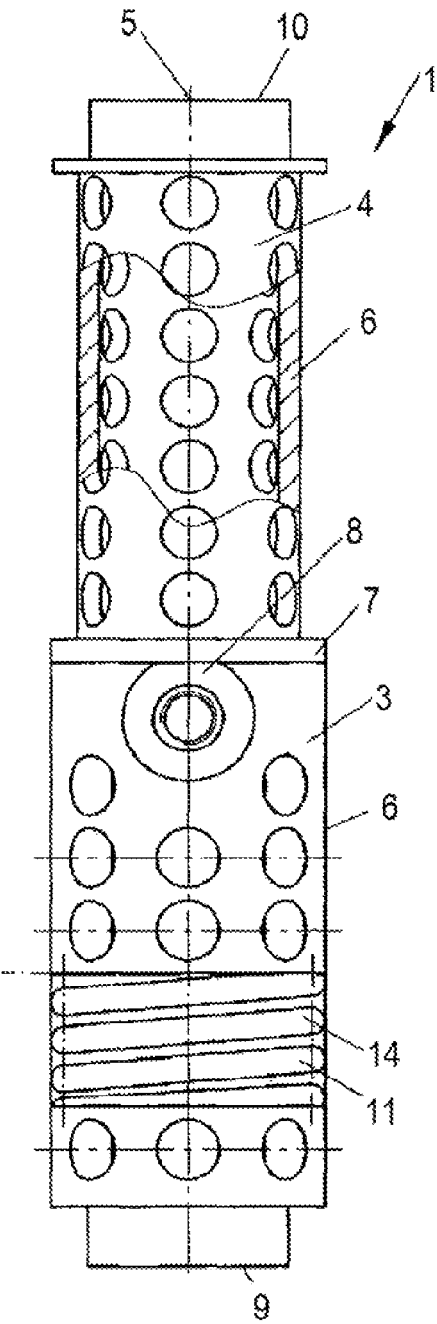
FIG. 4 is a view like FIG. 1 of an embodiment with a coil spring integrated into the wall of the sleeve.
Figure 7:
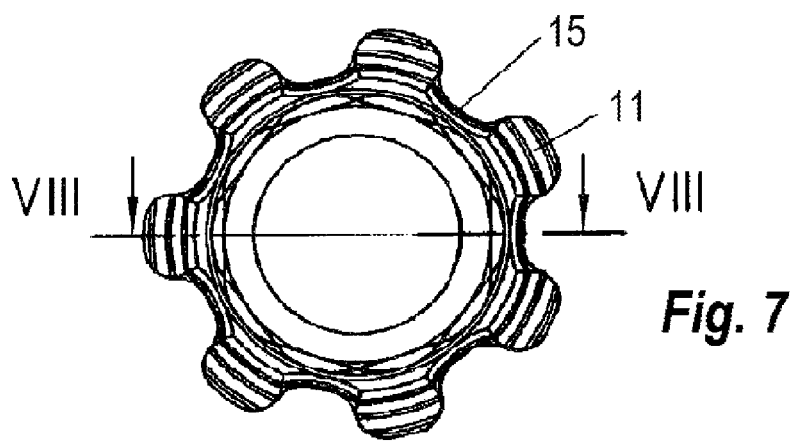
FIG. 7 is a plan view of an adapter plate with lamellae integrated into the surface thereof.
Figure 8:
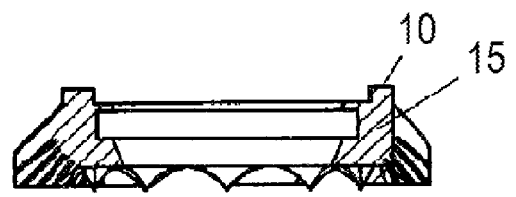
FIG. 8 is section VIII-VIII from FIG. 7.
Figure 9:
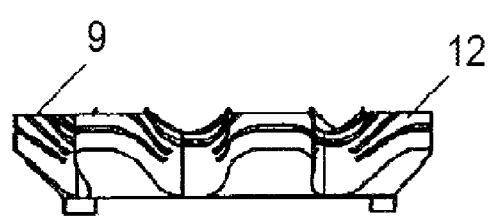
FIG. 9 is a side view of the adapter plate from FIG. 7.

It is therefore possible that the elastically compressible part 11 is formed from an elastically compact material 15 having lamellae 12. Another possibility is that the elastically compressible part 11 is provided in an elastic configuration (FIG. 18). FIG. 18 also shows that in addition an elastically compressible part 11 is integrated in the wall of the tubular sleeve 6, FIG. 18 further showing an arrangement with slots 13 that are formed in a crosswise offset arrangement, namely such that two diametrically opposite slots 13 are formed in a radial plane of the sleeve 6, which slots are offset by 90° to the longitudinal axis with respect to the slots 13 in the adjacent radial plane. As an alternative, FIG. 1 shows an embodiment of a honeycomb structure in the wall of the sleeve 6. FIG. 4 shows an illustrated embodiment with an integrated coil spring 14.

Furthermore, it should be pointed out that end adapter plates 15 can be assigned to the sleeves 6, which adapter plates form the first contact surface 9 and the second contact surface 10, the adapter plates 15 being also usable for forming the elastically compressible part 11, that can have, for example, a density gradient extending longitudinally of the sleeve 6 (FIG. 10).

Figure 15:
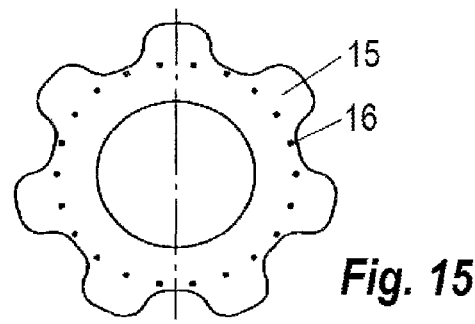
FIG. 15 is a further embodiment of an adapter plate with pins supported in a flexible pad.
Figure 12:
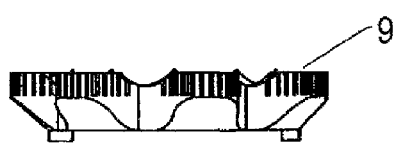
FIG. 12 is a side view of the adapter plate of FIG. 11.
Figure 16:
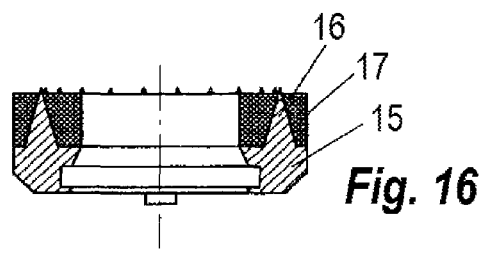
FIG. 16 is a longitudinal section through the adapter plate of FIG. 15.
Figure 13:
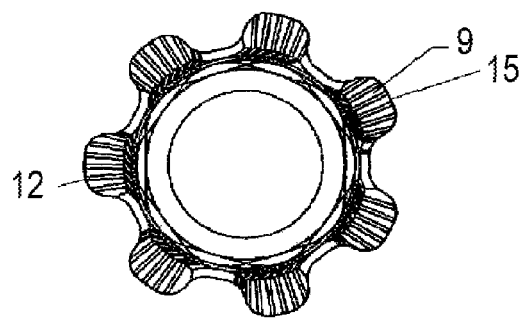
FIG. 13 is a further embodiment of an adapter plate in a view like FIG. 7.
Figure 17:
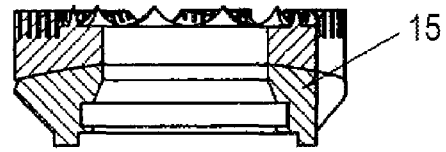
FIG. 17 is a longitudinal section through an adapter plate constructed in a two-part manner, comprising an upper shell and a lower shell, the upper shell has a lamella structure.
Figure 14:
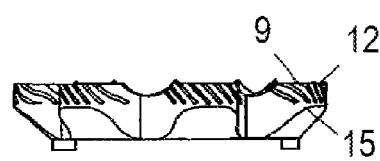
FIG. 14 is a side view of the adapter plate of FIG. 13

FIGS. 15 and 16 show embodiments in which adapter plates 15 carry respective pins 16 for bearing against the adjacent vertebrae 2, which pins are supported in a flexible pad 17.

The invention claimed is:

1. An implant for use between two adjacent spinal vertebrae, the implant comprising
    a first outer tubular sleeve extending along a longitudinal axis, having an axially outwardly directed first outer bearing surface engageable with one of the two vertebrae, and formed with an array of transversely extending and radially throughgoing slots imparting longitudinal elasticity to the first sleeve;
    a second inner tubular sleeve extending along the longitudinal axis, having a respective axially oppositely outwardly directed second outer bearing surface engageable with the other of the two vertebrae, having an external screwthread, and fittable coaxially in and slidable axially on the first sleeve; and
    a ring having an internal thread engaged with the external screwthread of the second sleeve and an array of external teeth, the ring bearing axially on the second outer tubular sleeve such that rotation of the ring on the first sleeve can axially shift the second sleeve axially relative to the first sleeve to change a length of the implant.

2. The implant defined in claim 1, further comprising:
a plurality of elastically compressible parts distributed uniformly over the first bearing surface or the second bearing surface and engageable between the respective bearing surfaces and the respective vertebrae.

3. The implant defined in claim 2, wherein the compressible parts are laminae.

4. The implant defined in claim 1, wherein the slots are arrayed in pairs diametrically opposite each other in respective radial planes of the sleeves, each pair of slots being offset by 90° to the longitudinal axis of the sleeve with respect to slots in the pairs in adjacent radial planes.

5. The implant defined in claim 1, further comprising:
respective end adapter plates on the sleeves and forming the first bearing surface and the second bearing surface.

6. The implant defined in claim 5, wherein the adapter plates carry respective pins that are supported in respective flexible pads engageable with the adjacent vertebrae.

7. The implant defined in claim 5, wherein the adapter plates are pivoted on the respective sleeves.

8. The implant defined in claim 1, further comprising:
a gear rotatable in the first sleeve about a radial axis and meshing with the teeth of the ring such that rotation of the gear about the radial axis rotates the ring about the longitudinal axis and thereby adjusts the length of the implant.

* * * * *